United States Patent [19]
Potyrailo et al.

[11] Patent Number: 6,166,804
[45] Date of Patent: Dec. 26, 2000

[54] METHOD AND APPARATUS FOR OBTAINING FLUORESCENCE DATA

[75] Inventors: Radislav Alexandrovich Potyrailo, Niskayuna; John Patrick Lemmon, Delanson, both of N.Y.

[73] Assignee: General Electric Company, Schenectady, N.Y.

[21] Appl. No.: 09/398,676

[22] Filed: Sep. 20, 1999

[51] Int. Cl.$^7$ .................................................. G01N 21/64
[52] U.S. Cl. ............................ 356/318; 356/73; 356/417; 250/458.1; 250/461.1
[58] Field of Search .............................. 356/73, 317, 318, 356/417, 445, 446; 250/458.1, 459.1, 461.1, 461.2

[56] References Cited

U.S. PATENT DOCUMENTS

| | | | |
|---|---|---|---|
| 5,822,072 | 10/1998 | Dai et al. | 385/12 |
| 5,974,211 | 10/1999 | Slater | 385/115 |
| 6,008,889 | 10/1998 | Zeng et al. | 356/73 |

OTHER PUBLICATIONS

Fuchs et al: "Combined Fluorescence and Reflectance Spectroscopy: In Vivo Assessment of Oral Cavity Epithelial Neoplasia", Lasers and Electro–Optics, 1998, CLEO 98. Technical Digest.Conference held on May 3–8 1998, pp. 306–307.

Spatially resolved analyte mapping with time–of–flight optical sensors, Radislav A. Potyrailo and Gary M. Hieftje, Trends in Analytical Chemistry, vol. 17, No. 10, 1998, pp. 593–604.

*Primary Examiner*—F. L. Evans
*Attorney, Agent, or Firm*—Noreen C. Johnson; Douglas E. Stoner

[57] ABSTRACT

In an exemplary embodiment, the apparatus includes an electromagnetic radiation source, an optical analyzer, and a fiber optic bundle. The fiber optic bundle has an excitation fiber in optical communication with the electromagnetic radiation source and a plurality of emission fibers in optical communication with the optical analyzer. The optical analyzer can have multiple channels, including a fluorescence-emission channel in optical communication with the emission fibers. Optionally, the fiber optic bundle can further contain at least one reflection fiber in optical communication with an absorbance/reflectance channel. In addition to detecting Fries product in formed polycarbonate materials, the method and apparatus can also be utilized to directly determine the concentration of a target species in parallel polycarbonate reactor systems.

27 Claims, 7 Drawing Sheets

METHOD AND APPARATUS FOR OBTAINING FLUORESCENCE DATA

BACKGROUND OF THE INVENTION

1. Field of the Invention

The present invention is directed to a method and apparatus for obtaining fluorescence data and, more specifically, to a method and apparatus for rapid in situ quantification of target species in a reactor.

2. Discussion of Related Art

Conventional industrial plants synthesize polycarbonate by mixing together an aqueous solution of a dihydroxy compound (e.g., bisphenol-A) with an organic solvent (e.g., dicloromethane) containing a carbonyl halide (e.g., phosgene). Upon mixing the immiscible organic and aqueous phases, the dihydroxy compound reacts with the carbonyl halide at the phase interface. Typically, a phase transfer catalyst, such as a tertiary amine, is added to the aqueous phase to enhance the reaction. This synthesis method is commonly known as the "interfacial" synthesis method for preparing polycarbonates, and the product of this synthesis is commonly known as LF grade polycarbonate.

The interfacial method for making polycarbonate has several inherent disadvantages. First, it can be a disadvantage to operate a process that requires phosgene as a reactant. Second, the process utilizes large amounts of an organic solvent, which can require expensive precautionary measures to prevent deleterious environmental effects. Third, the interfacial method requires significant capital investment in equipment. Fourth, polycarbonate produced by the interfacial process is prone to exhibiting inconsistent color, high levels of particulates, and high chloride concentration.

An alternate polycarbonate manufacturing method has been developed which avoids several of the aforementioned problems. This synthesis technique, commonly referred to as the "melt" process, involves the transesterification of a carbonate diester (e.g., diphenylcarbonate) with a dihydroxy compound (e.g., bisphenol-A). This reaction is typically performed without a solvent and is driven to completion by mixing the reactants under reduced pressure and high temperature with simultaneous distillation of the phenol produced by the reaction. Polycarbonate produced by the melt process is typically referred to as LX grade polycarbonate. The melt process provides many advantages over the interfacial process. More specifically, the melt process does not employ phosgene; it does not require a solvent; and it uses less equipment. Moreover, the polycarbonate produced by the melt process does not contain chlorine contamination from the reactants; it has lower particulate levels; and it has a more consistent color. Therefore, in certain circumstances, it can be highly desirable to use the melt process in production facilities.

However, the melt process tends to produce polycarbonate with significantly higher level of branching than that produced by the interfacial process. This branching is the result of a side reaction called the Fries rearrangement, which involves the conversion of a phenolic ester into corresponding ortho and para hydroxyketones. The rearrangement is based on the Fries rule, which postulates that the most stable form of a polynuclear compound is that arrangement which has the maximum number of rings in the benzenoid form.

The Fries rearrangement product in polycarbonate is typically the result of exposure to elevated temperatures in the presence of an active catalyst. The primary Fries product is a salicylate ester that, under melt polymerization conditions, can further react to form a tri-functional molecule that acts as a branch point for the resulting polymer. In this context, the generation of the Fries branch point structure can lead to polymer branching, thereby generating inconsistent melt behavior. In various applications, this branching significantly increases the ductility of the polycarbonate and is, therefore, undesirable.

As the demand for high performance materials has continued to grow, new and improved methods of providing improved products more economically are needed to supply the market. Due in part to the advantages inherent in polycarbonate production by the melt process, there is significant interest among industry members in producing LX grade polycarbonate with low Fries product content. In this context, various reactant and catalyst combinations for melt polymerization are constantly being evaluated; however, the identities of chemically or economically superior reactant systems for melt polymerization processes continue to elude the industry. As parallel screening gains popularity in all areas of chemistry, high-throughput screening of potential reactant systems will become increasingly important. As such, new and improved methods are needed for rapid, direct quantification of reaction products.

SUMMARY

Accordingly, the present invention is directed to a method and apparatus for obtaining fluorescence data from a specimen. In an exemplary embodiment, the apparatus includes an electromagnetic radiation source, an optical analyzer, and a fiber optic bundle. The fiber optic bundle has an excitation fiber in optical communication with the electromagnetic radiation source and a plurality of emission fibers in optical communication with the optical analyzer. The optical analyzer can have multiple channels, including a fluorescence-emission channel in optical communication with the emission fibers. Optionally, the fiber optic bundle can further contain at least one reflection fiber in optical communication with an absorbance/reflectance channel. In addition to detecting Fries product in formed polycarbonate materials, the method and apparatus can also be utilized to directly determine the concentration of a target species in parallel polycarbonate reactor systems.

BRIEF DESCRIPTION OF THE DRAWINGS

Various features, aspects, and advantages of the present invention will become more apparent with reference to the following description, appended claims, and accompanying drawings, wherein

DETAILED DESCRIPTION

Figure 1:
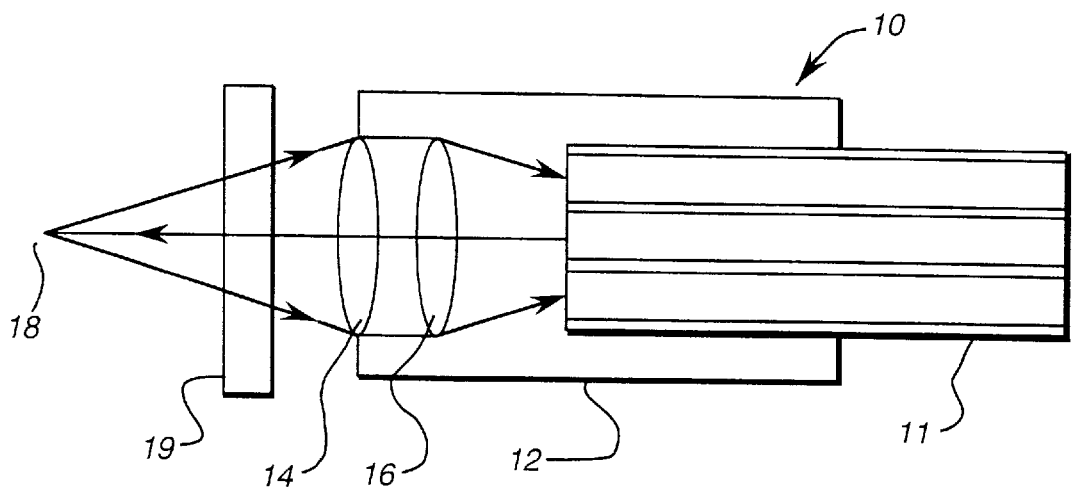
FIG. 1 is a schematic view of an aspect of an embodiment of the present invention.

Terms used herein are employed in their accepted sense or are defined. In this context, the present invention is directed to a method and apparatus for obtaining fluorescence data. It is contemplated that the method and apparatus can be especially useful, inter alia, for directly determining the concentration of a target species in a composition comprising aromatic carbonate chain units. Such a composition may be the product of a melt polymerization reaction or an interfacial polymerization reaction. The method may be performed during a reaction or upon the final product of the reaction. It is further contemplated that the method and apparatus can be used on polycarbonate compositions that have been subjected to further processing. The method is capable of determining the concentration of a target species, such as Fries product or the like, by direct fluorescence measurements. The direct analytical method can be performed on polycarbonate compositions in various forms including, for example, films, pellets, sheets, solutions, suspensions, or blends containing polycarbonate.

In various embodiments, the disclosed method and apparatus eliminates the need for extensive sample preparation as required by other detection methods. For example, polycarbonate depolymerization followed by liquid chromatography analysis requires a time consuming (30–60 minutes) sample preparation step involving dissolution of the polycarbonate. Likewise, it can take 2 hours or more to complete a single measurement using NMR methodology, thereby effectively eliminating the opportunity to quantify a target species in real time during a reaction or in connection with parallel combinatorial screening.

As used herein, the terms "polycarbonate", "polycarbonate composition", and "composition comprising aromatic carbonate chain units" includes compositions having structural units of the formula (I):

(I)

in which at least about 60 percent of the total number of $R^6$ groups are aromatic organic radicals and the balance thereof are aliphatic, alicyclic, or aromatic radicals.

Preferably, $R^6$ is an aromatic organic radical and, more preferably, a radical of the formula (II):

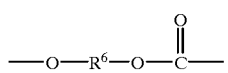 (II)

wherein each of $A^1$ and $A^2$ is a monocyclic divalent aryl radical and $Y^1$ is a bridging radical having one or two atoms which separate $A^1$ from $A^2$. In an exemplary embodiment, one atom separates $A^1$ from $A^2$. Illustrative non-limiting examples of radicals of this type are —O—, —S—, —S(O)— or —S(O$_2$)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical Y can be a hydrocarbon group or a saturated hydrocarbon group such as methylene, cyclohexylidene or isopropylidene.

Polycarbonates can be derived from dihydroxy compounds in which only one atom separates $A^1$ and $A^2$. As used herein, the term "dihydroxy compound" includes, for example, bisphenol compounds representative of general formula (III) as follows:

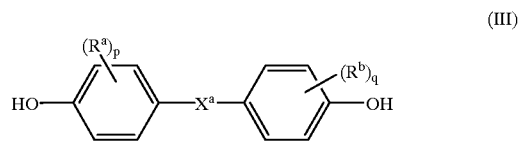
(III)

In formula (III), $R^a$ and $R^b$ each represent a halogen atom or a monovalent hydrocarbon group and may be the same or different. The p and q variables represent integers from 0 to 4. The $X^a$ variable represents one of the following groups:

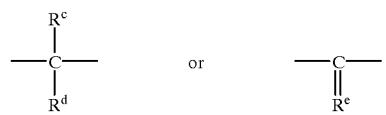

Variables $R^c$ and $R^d$ each independently represent a hydrogen atom or a monovalent hydrocarbon group. Variables $R^c$ and $R^d$ may form a ring structure. Variable $R^e$ is a divalent hydrocarbon group.

Some illustrative, non-limiting examples of suitable dihydroxy compounds include the dihydroxy-substituted aromatic hydrocarbons disclosed by name or formula (generic or specific) in U.S. Pat. No. 4,217,438. A nonexclusive list of specific examples of the types of bisphenol compounds that may be represented by formula (III) includes the following:

1,1-bis(4-hydroxyphenyl) methane;
1,1-bis(4-hydroxyphenyl) ethane;
2,2-bis(4-hydroxyphenyl) propane (hereinafter referred to as "bisphenol A" or "BPA");
2,2-bis(4-hydroxyphenyl) butane;
2,2-bis(4-hydroxyphenyl) octane;
1,1-bis(4-hydroxyphenyl) propane;
1,1-bis(4-hydroxyphenyl) n-butane;
bis(4-hydroxyphenyl) phenylmethane;
2,2-bis(4-hydroxy-1-methylphenyl) propane;
1,1-bis(4-hydroxy-t-butylphenyl) propane;
bis(hydroxyaryl) alkanes such as 2,2-bis(4-hydroxy-3-bromophenyl) propane;
1,1-bis(4-hydroxyphenyl) cyclopentane; and
bis(hydroxyaryl) cycloalkanes such as 1,1-bis(4-hydroxyphenyl) cyclohexane.

Preferred LX polycarbonates are bisphenol A polycarbonates, in which each of $A^1$ and $A^2$ is p-phenylene and Y is isopropylidene. Preferably, the average molecular weight of the initial polycarbonate ranges from about 5,000 to about 100,000; more preferably from about 10,000 to about 65,000, and most preferably from about 15,000 to about 35,000.

In monitoring and evaluating polycarbonate synthesis, it is of particular interest to determine the concentration of Fries product present in the polycarbonate.

As noted, the generation of significant Fries product can lead to polymer branching, resulting in uncontrollable melt behavior. As used herein, the terms "Fries" and "Fries product" denote a repeating unit in polycarbonate having the following formula:

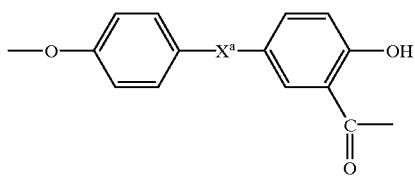

wherein $X^a$ is a bivalent radical as described in connection with Formula (III) supra.

A portion of an exemplary embodiment of the apparatus is shown in FIG. 1. The portion shown is an optical probe 10, wherein a fiber optic bundle 11 is partially enclosed within a probe housing 12. A focusing lens 14 and a collimating lens 16 are also disposed within probe housing 12. In the embodiment shown in FIG. 2, fiber optic bundle 11 comprises a plurality of emission fibers 52, which are disposed around an excitation fiber 54. The excitation fiber is placed in optical communication with an electromagnetic radiation source (not shown), and the emission fibers are placed in optical communication with an optical analyzer (not shown). In operation, an excitation signal passes through excitation fiber 54 and into a specimen 18 (FIG. 1). The specimen emits an emission signal, which passes through emission fibers 52 and to the optical analyzer. In an exemplary embodiment, the apparatus is used to obtain fluorescence data from reaction products during the course of a reaction, which requires optical access to the reaction zone through a viewing window 19 (FIG. 1), a translucent reactor wall, or the like.

The configuration shown provides increased signal levels at significant distances from the probe. Conventional fluorescence probes for remote monitoring utilize a single optical fiber or a bifurcated fiber-optic bundle. To make a measurement, an excitation light is delivered from a source to a target location. Emission from the target is collected with the same or another fiber or fibers and guided to a detector which measures fluorescence signal (intensity or lifetime). In such a design, the excitation light leaves the excitation fiber or fibers as a cone defined by the numerical aperture of the fiber. Fluorescence emission is captured by the numerical aperture of the same or another fiber or fibers. While, with the conventional configuration, a large sample volume is illuminated, this does not lead to an appreciable fluorescence signal at distances beyond several millimeters from the fiber tip. Thick polymer films which are typically deposited on all surfaces of a reactor during polymerization prevents the use of the conventional configuration to obtain accurate fluorescence measurements, even if a fluorescence probe is located within the reaction zone.

Figure 3:
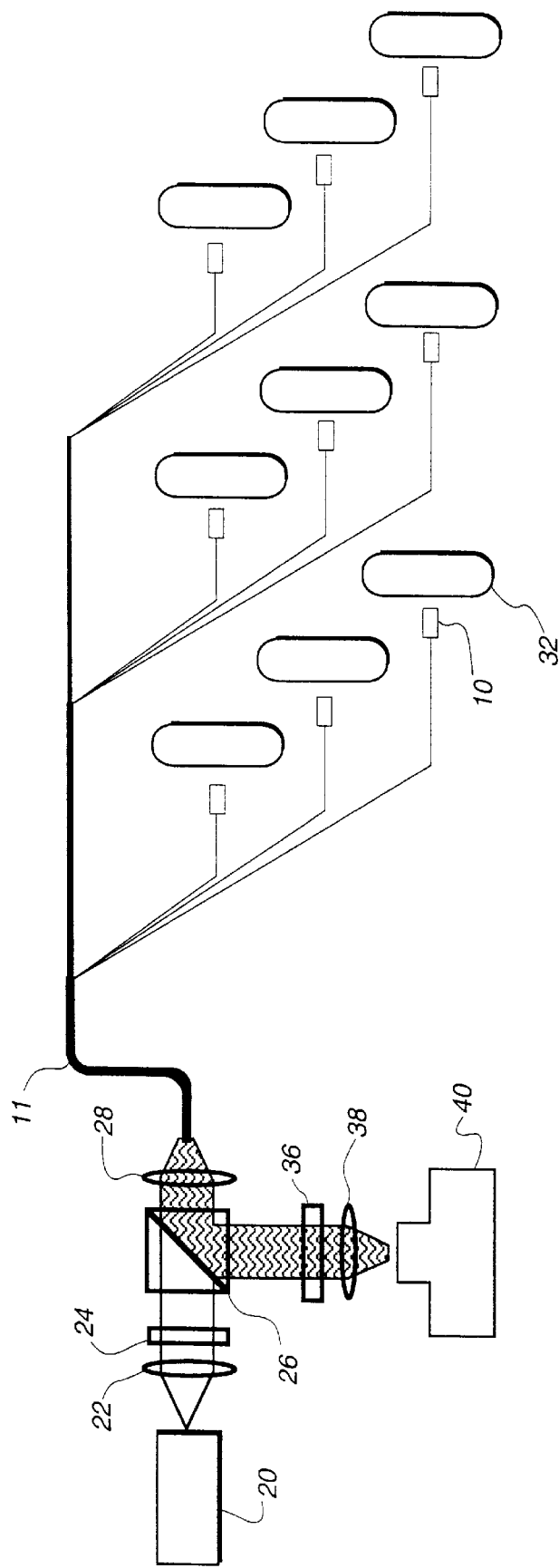
FIG. 3 is a schematic view of an aspect of an embodiment of the present invention.

An embodiment of the apparatus of the present invention is presented in FIG. 3. The apparatus is useful for parallel monitoring of Fries product in multiple polymerization reactors and the like. It is contemplated that the apparatus shown can also be useful for combinatorial screening of catalysts and the like. The apparatus includes a white light source 20, a collimator 22, an excitation optical filter 24, a beam splitter 26, a focusing lens 28, a fiber optic bundle 11, a plurality of polymerization reactors 32, and a plurality of optical probes 10 (as described supra), an emission optical filter 36, a second focusing lens 38, and an imaging photo-detector 40.

Figure 5:
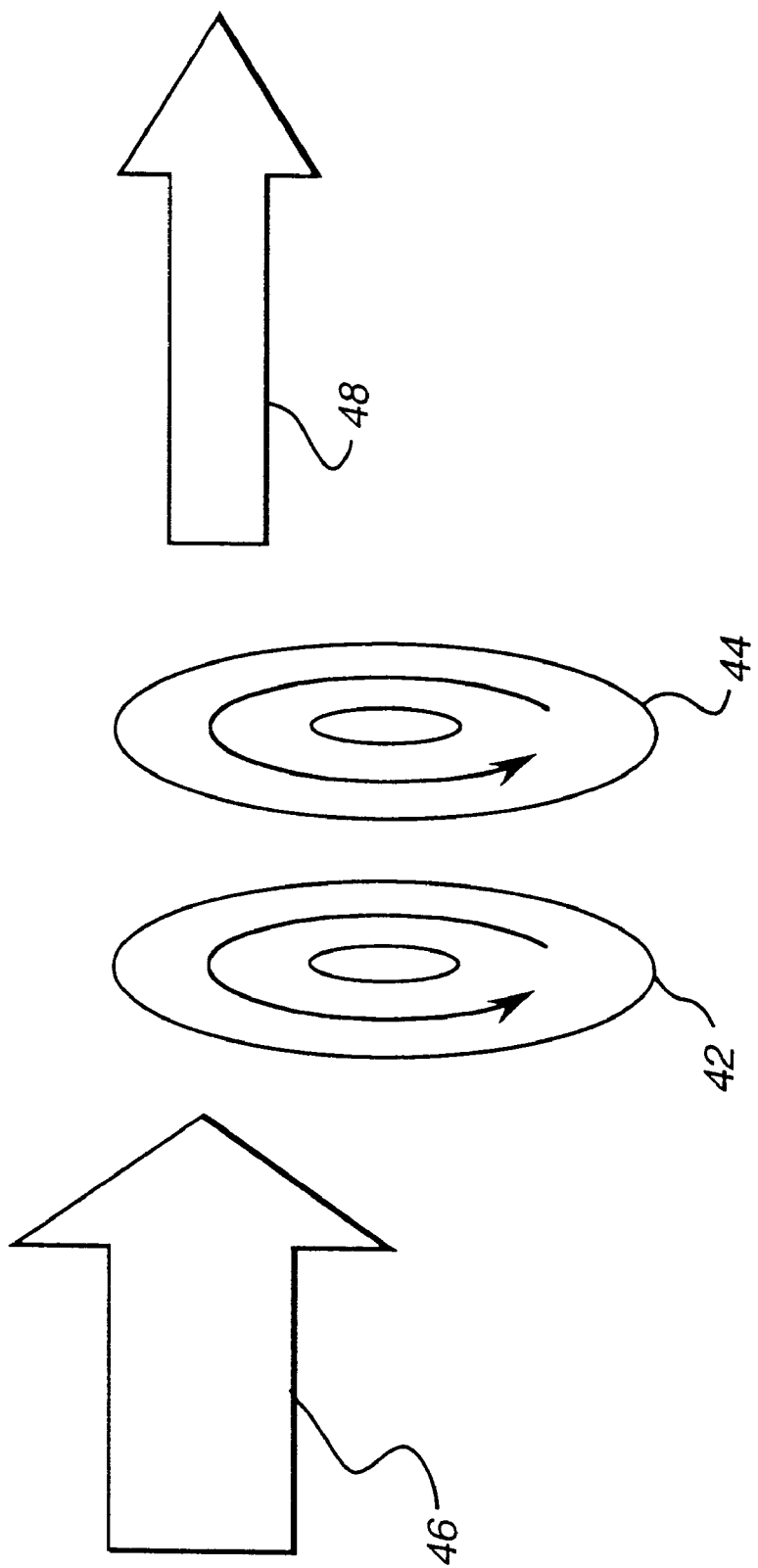
FIG. 5 is a schematic view of an aspect of an embodiment of the present invention.

In operation, polymerization reactions are carried out in polymerization reactors 32 to produce polycarbonate. White light from source 20 is collimated and passed through excitation optical filter 24. As shown in FIG. 5, both excitation optical filter 24 and emission optical filter 36 preferably comprise two filter elements 42, 44 with each of the filter elements having a continuous linear variation of either cut-on or cut-off wavelength. Such optical filter elements are commercially available, for example, from Coherent, Inc. of Auburn, Calif. White light 46 can be converted to colored light by using an opposed pair of these filter elements. The bandwidth of white light 46 can be adjusted by counter rotating the elements, while coordinated rotation changes the center wavelength. In this manner, incoming white light 46 can be converted to constant-bandwidth, variable wavelength output light 48. With reference the FIG. 3, the filtered light passes through beam splitter 26 and is focused onto the tip of fiber-optic bundle 11. Light travels through excitation fiber 54 (FIG. 2) of fiber-optic bundle 11 and is delivered to the reaction zone via optical probes 10.

The emission signal passes through emission fibers 52 and is directed through beam splitter 26 and emission optical filter 36 having variable edge-pass optical filter elements 42, 44 (FIG. 5) before being focused into imaging photo-detector 40, such as, e.g., a CCD camera or the like. Depending on the relative position of filter elements 42, 44 in each filter, excitation-emission fluorescence matrices can be collected simultaneously from each reactor 32. When excitation optical filter 24 is set to transmit white light, the absorbance/reflectance spectra are collected from each reactor 32 by the coordinated rotation of emission filter elements 42, 44. Imaging photo-detector 40 is used for monitoring the fluorescence at each of the multiple measurement locations.

Figure 2:
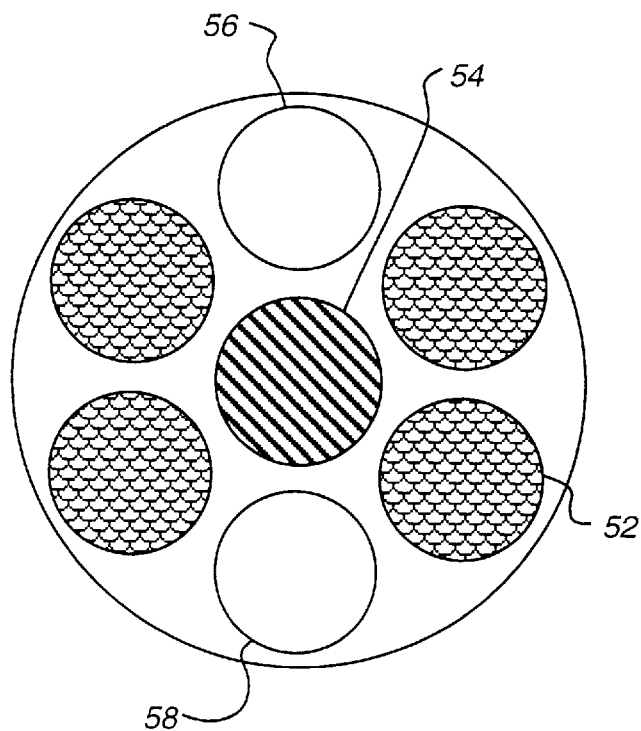
FIG. 2 is a cross-sectional view of an aspect of an embodiment of the present invention.

With reference to FIG. 2, fiber optic bundle 11 can be provided with an optional third fiber 56 to deliver white light to a measurement location while one or more reflectance fibers 58 can be provided to deliver the back propagated portion of light to an optical analyzer. These absorption/reflection measurements can be used to compensate for variations in fluorescence signal due to primary and secondary inner filter effects. The configuration of the probe allows excitation and absorbance/reflection measurements to be obtained in rapid sequence without changing the position of any portion of the apparatus relative to the specimen, thereby allowing effective real time monitoring of the specimen.

As used herein, the term "inner filter effect" includes the significant absorption of the excitation or emission radiation as the radiation travels through the medium where the target species is located. More specifically, "primary inner filter effect" denotes significant absorption of the excitation radiation, and "secondary inner filter effect" denotes significant absorption of the emission radiation. As known to those skilled in the art, inner filter effects can affect the relationship between luminescence signal and analyte concentration, and correction factors can be calculated from absorbance and scatter at the excitation and emission wavelengths in order to compensate for the loss of optical signal at these wavelengths. Use of the probe shown in FIGS. 1 and 2 can also compensate for variations in the refractive index of the optical medium.

Figure 4:
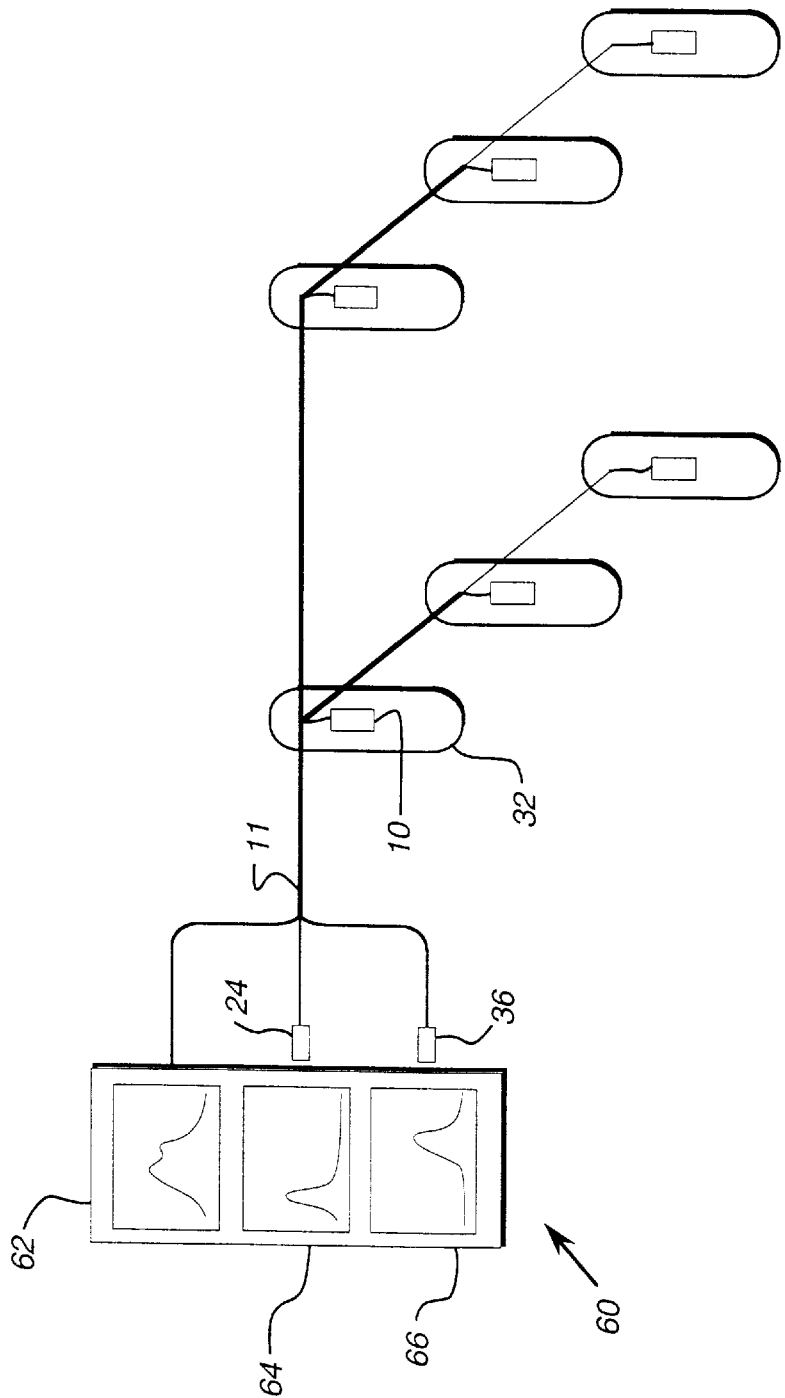
FIG. 4 is a schematic view of an aspect of an embodiment of the present invention.

Another apparatus for parallel on-line monitoring of Fries product in multiple polymerization reactors is shown in FIG. 4. The apparatus includes a multichannel spectrometer 60 having an absorbance/reflectance channel 62, a fluorescence-excitation channel 64, and a fluorescence-emission channel 66. A fiber-optic bundle 11 is placed in optical communication with spectrometer 60 and a plurality of optical probes 10 (as described above), which can be located proximate reactors 32 (non-invasive) or immersed in reactors 32 (invasive, as shown). Two of the channels 64, 66 are provided with optical filters 24, 36 (described supra). Emission fibers 52 are placed in optical communication with fluorescence-emission channel 66. Reflectance fiber 58 is placed in optical communication with absorbance/reflectance channel 62.

In operation, multichannel spectrometer 60 is capable of measuring the excitation and emission fluorescence spectra and absorbance/reflectance from each reactor 32 in rapid sequence. Measurements in multiple reactors can be accomplished using the art-recognized time-domain multiplexing approach or having a miniature spectrometer for each of the reactors.

In exemplary embodiments, the present method is capable of directly determining the concentration of a target species (e.g., Fries product) in a composition comprising aromatic carbonate chain units. The method includes the steps of providing an apparatus having an electromagnetic radiation source, an optical analyzer, and a fiber optic bundle. The bundle contains an excitation fiber in optical communication with the electromagnetic radiation source and a plurality of emission fibers in optical communication with the optical analyzer. A portion of the composition is irradiated with electromagnetic radiation at an excitation wavelength sufficient to cause the target species to emit a fluorescence spectrum. The method further includes the steps of detecting at least a portion of the fluorescence spectrum and determining the concentration of the target species from the fluorescence spectrum.

In order to provide adequate quantification of the target species, the composition is preferably irradiated at an excitation wavelength that allows the target species to fluoresce at a detectable level that provides differential emission between the target species and interfering species. The present method permits quantification of Fries product during a melt polymerization reaction in the presence of fluorescent, absorbing, and scattering interfering species. The conditions used allow for selective excitation of the Fries product in the polycarbonate material; collection of its fluorescence emission; and relation of the measured fluorescence signal to Fries concentration. The range of excitation wavelengths for quantification of Fries product is preferably selected to satisfy at least two criteria: (1) appreciable absorbance of the selected excitation wavelengths by Fries product and (2) minimal absorbance of the selected excitation wavelengths by interfering species. The range of emission wavelengths for quantification of Fries product is preferably selected to satisfy at least two criteria: (1) Fries product emits fluorescence and (2) interfering species do not appreciably emit fluorescence.

Figure 6:
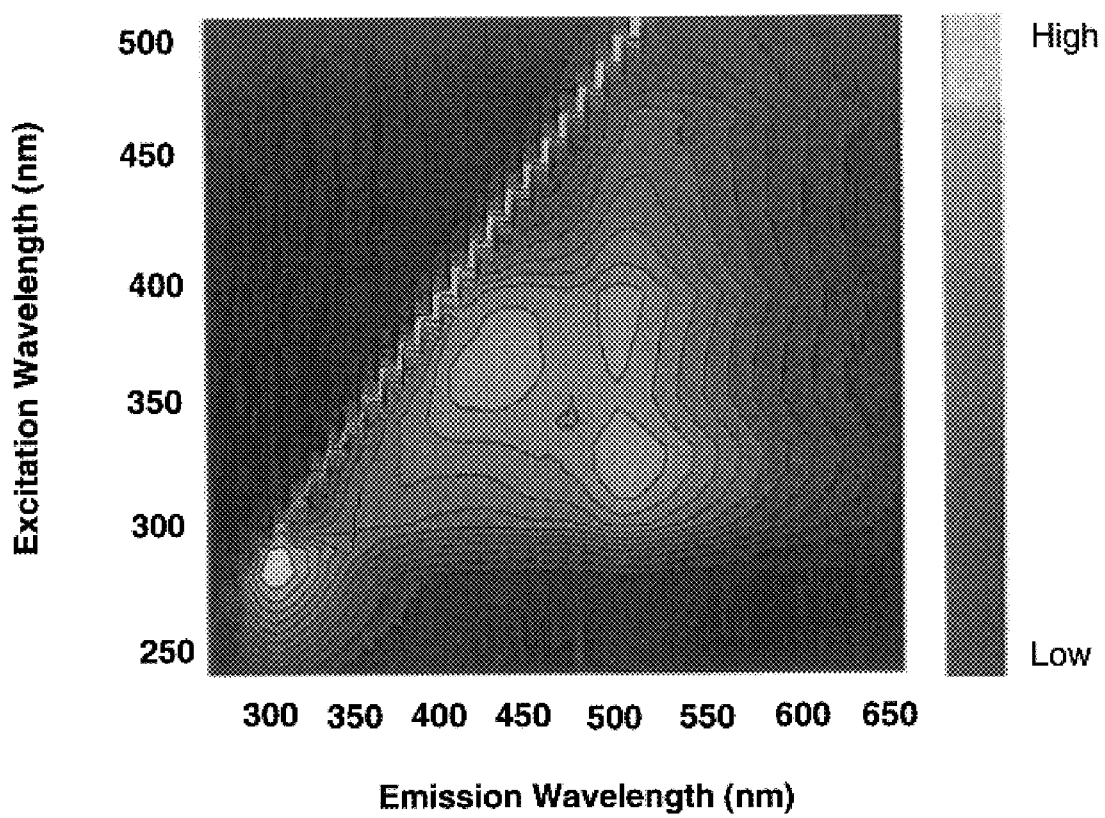
FIG. 6 is an excitation-emission spectrum of solid LX melt polycarbonate.

In addition to Fries product, which produces detectable fluorescence signal, there are several possible interfering species in LX material. Exemplary interfering species include non-branched Fries end-groups, non-Fries end-groups, and cyclics. Also, different contaminant species may potentially emit fluorescence. A typical excitation-emission spectrum of a solid LX material (119 ppm of Fries product) is presented in FIG. 6 to illustrate the complexity of the fluorescence spectrum of a solid LX material obtained after a melt polymerization reaction. When dealing with Fries product as the target species, a suitable excitation wavelength is between about 250 nm and about 500 nm; preferably between about 300 nm and about 400 nm; more preferably between about 320 nm and about 350 nm; and most preferable about 340 nm. Other portions of the excitation and emission fluorescence spectra can be collected for calibration, normalization, and scaling purposes.

Compensation for the variation in absorbance and scattering effects of the measured regions at the excitation and emission wavelengths can be accomplished by at least two compensation methods. The first compensation method comprises measuring the absorption spectrum of the probed region of polycarbonate over the spectral range that covers the excitation and emission wavelengths. The second compensation method comprises using second order Rayleigh scattering effects in the emission and excitation spectra for scaling the spectral features.

In real-time monitoring situations, the collected fluorescence intensity can be affected by a number of instrumental and sample parameters not related to the concentration of the fluorescent product. However, various embodiments of the disclosed method allow for compensation to provide reproducible signals from single or multiple polymerization reactors during monitoring of the progress of, e.g., a polycarbonate melt polymerization reaction.

Figure 7:
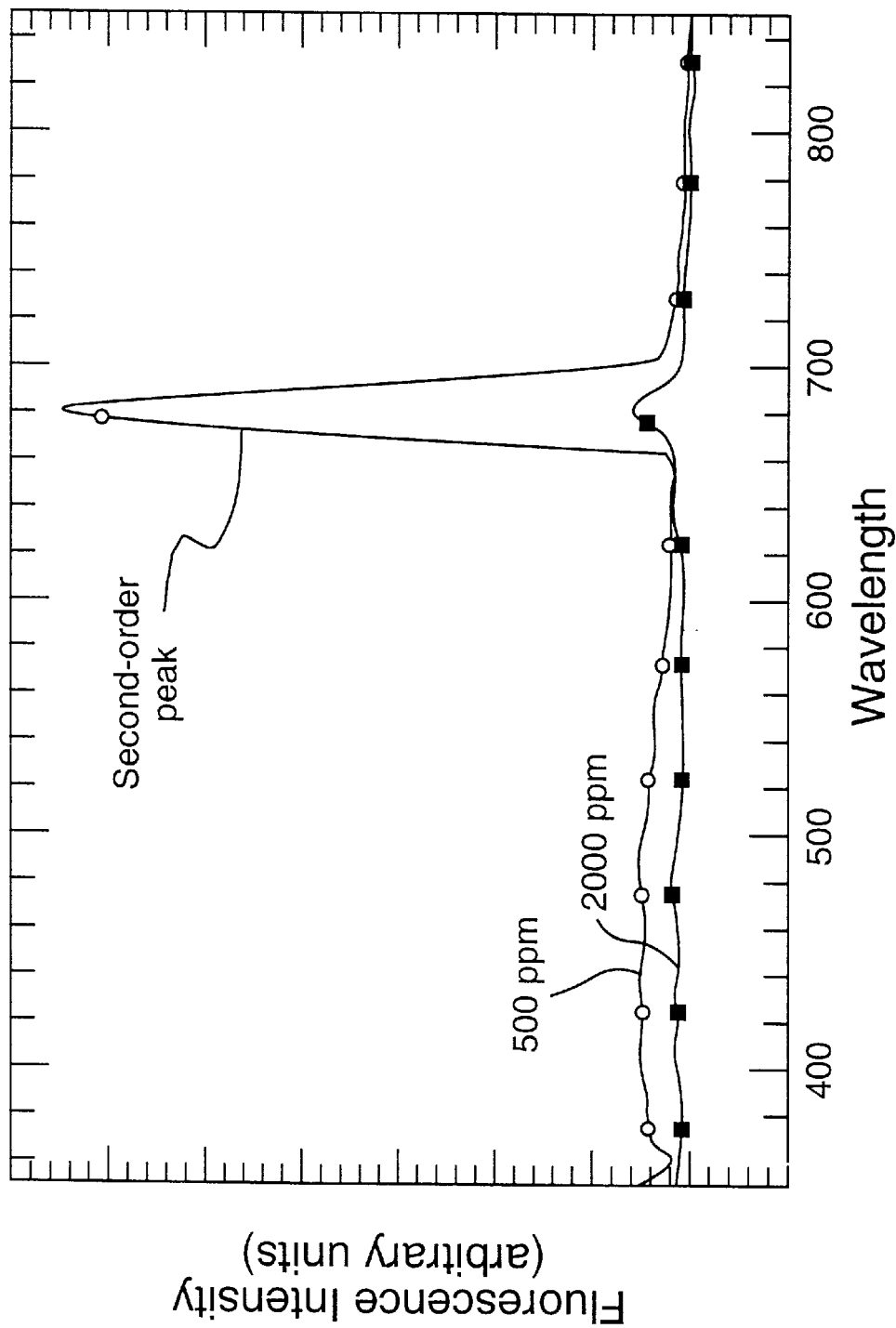
FIG. 7 is a graphical representation of fluorescence spectra of various concentrations of Fries product in polycarbonate.
Figure 8:
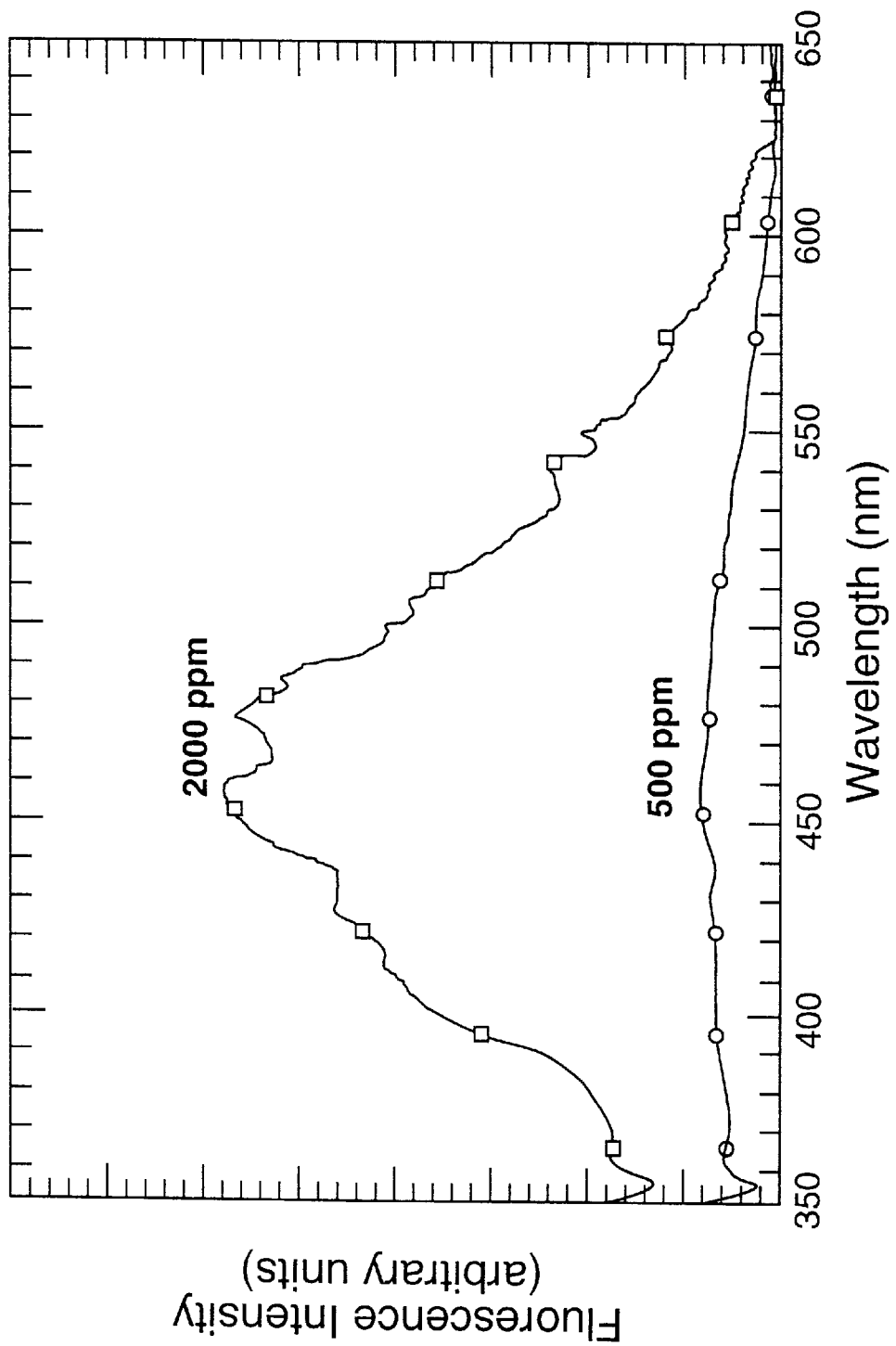
FIG. 8 is a graphical representation of fluorescence spectra of various concentrations of Fries product in polycarbonate.

Second-order Rayleigh scattering effects are typically undesirable in conventional spectrometers for general applications because they distort the true spectral features of the measured samples. These second order effects in the emission and excitation spectra can be eliminated by various techniques. For example, it is common to use excitation and emission filters that block the respective spectral portion of radiation from entering the measurement device (spectrometer). However, in various alternative embodiments of the present method, second order effects are used to scale spectral features. An example of second-order effects is shown in FIG. 7, where the peaks at 680 nm in both recorded spectra of solid polycarbonate samples are second-order effects resulting from excitation at 340 nm. These second order peaks are measured and used as reference excitation intensity. As shown in FIG. 7, the intensities of these peaks are different due to different excitation conditions of the two samples. However, as shown in FIG. 8, after scaling both second-order peaks to the same height, the resulting spectra for two different concentrations of Fries product can be readily compared. In this manner a measurement taken during or after a reaction can be compared to a standard measurement or to a measurement taken earlier in the reaction cycle.

It will be understood that each of the elements described above, or two or more together, may also find utility in applications differing from the types described herein. While the invention has been illustrated and described as embodied in a method and apparatus for obtaining fluorescence data, it is not intended to be limited to the details shown, since various modifications and substitutions can be made without departing in any way from the spirit of the present invention. For example, computer programs may be used to operate the apparatus and various other types of screening methods may be used in conjunction with the present method. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. An apparatus for obtaining fluorescence data from a specimen, said apparatus comprising
   (a) an electromagnetic radiation source;
   (b) a multi-channel optical analyzer having a fluorescence-emission channel and an absorbance/reflectance channel;
   (c) a fiber optic bundle having an excitation fiber in optical communication with said electromagnetic radiation source, at least one reflectance fiber in optical communication with said absorbance/reflectance channel, and a plurality of emission fibers in optical communication with said fluorescence-emission channel; and (d) a focusing lens disposed between said fiber optic bundle and said specimen.

2. The apparatus of claim 1, further comprising a collimating lens disposed between said focusing lens and said fiber optic bundle.

3. The apparatus of claim 2, wherein said fiber optic bundle, said focusing lens, and said collimating lens are configured and positioned relative to each other such that excitation and reflectance data can be obtained in rapid sequence without changing the position of any portion of the apparatus relative to the specimen.

4. The apparatus of claim 3, wherein said excitation fiber is disposed substantially along the central longitudinal axis of the fiber optic bundle with all other fibers located along the circumference of said excitation fiber.

5. A method of directly determining the concentration of a target species in a composition comprising aromatic carbonate chain units, said method comprising the steps of:

(a) providing an apparatus comprising an electromagnetic radiation source, an optical analyzer, and a fiber optic bundle having an excitation fiber in optical communication with said electromagnetic radiation source and a plurality of emission fibers in optical communication with said optical analyzer;

(b) irradiating a portion of said composition with electromagnetic radiation at an excitation wavelength sufficient to cause said target species to emit a fluorescence spectrum;

(c) detecting at least a portion of said fluorescence spectrum; and (d) determining the concentration of said target species from said fluorescence spectrum.

6. The method of claim 5, wherein said target species is a thermal Fries product.

7. The method of claim 6, wherein said composition is irradiated at an excitation wavelength that allows said Fries product to fluoresce at a detectable level that provides differential emission between said Fries product and interfering species.

8. The method of claim 7, wherein said excitation wavelength is between about 250 nm and about 500 nm.

9. The method of claim 8, wherein said excitation wavelength is between about 300 nm and about 400 nm.

10. The method of claim 9, wherein said excitation wavelength is between about 320 nm and about 350 nm.

11. The method of claim 10, wherein said excitation wavelength is about 340 nm.

12. The method of claim 5, wherein steps (a) and (b) occur during a polycarbonate reaction in a reactor system.

13. The method of claim 12, wherein steps (a) and (b) occur without removing any of said composition from said reactor system.

14. The method of claim 5, wherein steps (a) and (b) occur during a melt polycarbonate reaction.

15. The method of claim 6, wherein steps (a) and (b) occur during a melt polycarbonate reaction.

16. The method of claim 5, wherein said composition is a polycarbonate resin.

17. The method of claim 5, wherein said composition is a polycarbonate blend.

18. The method of claim 5, wherein said composition is in the form of a film.

19. The method of claim 5, wherein said composition is in the form of a sheet.

20. The method of claim 5, wherein said composition is in the form of a solution.

21. A method of determining the concentration of a target species in a composition comprising aromatic carbonate chain units during a polycarbonate reaction, said method comprising the steps of:

(a) providing an apparatus comprising an electromagnetic radiation source, an optical analyzer, a fiber optic bundle having an excitation fiber in optical communication with said electromagnetic radiation source and a plurality of emission fibers in optical communication with said optical analyzer;

(b) providing a first emission spectrum of said target species containing an initial second order Rayleigh scatter peak;

(c) exciting said target species with electromagnetic radiation;

(d) detecting the emission intensity of said target species to provide a second emission spectrum containing another second order Rayleigh scatter peak;

(e) scaling said first and second spectra such that said second order Rayleigh scatter peaks are the same height; and (f) determining the concentration of said target species.

22. The method of claim 21, wherein said target species is a thermal Fries product.

23. The method of claim 21, wherein both emission spectra are obtained during the course of a reaction.

24. The method of claim 22, wherein said composition is excited with electromagnetic radiation at a wavelength that allows said Fries product to fluoresce at a detectable level to provide differential emission between said Fries product and interfering species.

25. The method of claim 24, wherein said excitation wavelength is between about 300 nm and about 400 nm.

26. The method of claim 25, wherein said excitation wavelength is between about 320 nm and about 350 nm.

27. The method of claim 26, wherein said excitation wavelength is about 340 nm.

* * * * *